United States Patent

Heard et al.

[11] Patent Number: 6,115,625
[45] Date of Patent: Sep. 5, 2000

[54] MEDICAL ELECTRODE

[75] Inventors: Steve Heard, Escondido; Jens Axelgaard, Fallbrook, both of Calif.

[73] Assignee: Axelgaard Manufacturing Co., Ltd., Fallbrook, Calif.

[21] Appl. No.: 09/245,641

[22] Filed: Feb. 8, 1999

[51] Int. Cl.[7] .............................. A61B 5/0408; A61N 1/04
[52] U.S. Cl. ...................... 600/391; 600/395; 607/149; 607/152; 252/500
[58] Field of Search ...................... 600/391, 392, 600/395, 397; 607/149, 152; 606/32; 252/500

[56] References Cited

U.S. PATENT DOCUMENTS 5,868,136  2/1999  Fox et al. ................................. 600/397

Primary Examiner—Lee Cohen
Attorney, Agent, or Firm—Walter A. Hackler

[57] ABSTRACT

An electrode providing electrical contact with a patient's skin includes a conductive member adapted for connection to an external electrical apparatus and a non-liquid film for electrically interfacing to said patient's skin, the liquid film being electrically and mechanically connected to said conductive member. The non-liquid film includes an electrically conductive organic polymer plasticized with a polyhydric alcohol with said organic polymer being derived from a monomeric mixture comprising from about 15 to 30 pph acrylic acid, 0.5 to 30 pph N-vinylpyrrolidone and 0.01 to 2 pph of a crosslinking agent. The monomeric mixture may further comprise from about 0.5 to 8 pph of a thickening agent selected from the group consisting of N-vinylpyrrolidone/acrylic acid copolymers and N-vinylpyrrolidone/vinylacetate.

22 Claims, 1 Drawing Sheet

MEDICAL ELECTRODE

FIELD OF THE INVENTION

The present invention provides a combination electrode for use in medical applications, e.g., medical applications requiring monitoring and stimulation, having an electrical current conductor including a connector in addition to a skin-interfacing film wherein this film may have adhesive, plastic and hydrophilic properties such as may reside in an electrically conductive, polymeric composition.

BACKGROUND OF THE ART

Medical electrodes have, in the past, taken many shapes and forms. Principally, they have been shaped according to the use for which they are intended. Electrodes used with monitoring apparatus, such as EKG and EEG machines, commonly have small round contact surfaces, whereas electrodes used with such stimulation apparatus as pain control devices tend to be larger and have rectangularly and other conveniently shaped contact surfaces. Whether intended for monitoring or stimulation use, a design objective for each electrode group has been, and continues to be, good electrical signal transmission between a patient's skin surface and the electrical cables connected to a particular piece of apparatus. With respect to stimulation and monitoring electrodes, efficient signal transmission across the epidermis conductor interface is desirable. Further, with respect to stimulation electrodes, effective signal transmission free of current concentration points or "hot spots" is also desirable.

Of the electrodes presently available, many offer combination structures including a metallic or otherwise conductive support member to which an electrical wire from an associated apparatus may be attached.

Certain of the currently available electrodes, including electrical stimulation electrodes are disclosed in U.S. Pat. Nos. 4,722,354; 4,736,752; 4,819,328; 5,038,796 and 5,450,845 to Axelgaard et al which are hereby incorporated by reference to show various electrode designs including but not limited to medical electrode shapes, structures, materials and methods for connecting said medical electrodes to the appropriate electrical apparatus.

In many instances, the medical electrodes of the prior art need the addition of generous amounts of an electrode paste or gel applied directly to the conductive support member to enhance conductivity across the skin-electrode interface to the point where acceptable operating conditions are achieved.

Other prior art electrodes teach the incorporation of an open cellular skin interface pad secured to a conductive support member. This pad, as shown in U.S. Pat. No. 3,817,252, is often sponge material which functions to hold an amount of electrolyte solution in order to enhance conductivity across the skin-pad interface. Such an interface pad can be, alternately, saturated with electrode pastes or gels of the type that do not run or evaporate as readily as electrolyte solutions.

The prior art electrodes that require an electrode paste or gel or electrolyte solution provide a structure which does not always maintain constant, efficient and effective electrical transmission for long periods of time without the need for additional electrode paste, gel or solution. Moreover, there is a tendency while using these electrodes, for the electrode gel to separate and/or to flow to a nonuniform thickness. Under these conditions, sections of the conductive support member could be exposed to the skin and local hot spots can result which can cause discomfort if not severe enough to cause burns to the patient's skin. Therefore, medical electrodes wherein the adhesive, itself, provides the conductive interface between the skin and the electrical connector are very desirable. An electrode of this type is disclosed in U.S. Pat. No. 4,066,078 to Berg. In this patent, the polymer itself acts as the adhesive and, through the quaternary groups attached to the polymer backbone, provides a conductive interface.

Nevertheless, others have continued to formulate adhesive materials that effectively adhere to the skin and the materials that can be utilized in fabricating a medical electrode and also provide adequate conductivity. See, for example, U.S. Pat. Nos. 4,830,776; 4,274,420; 4,777,954; 4,699,146; 4,458,696; 5,024,227; 4,243,051; etc., which exemplify the continuing search for conductive adhesive materials for use in medical electrodes.

An objective of this invention, therefore, is to provide an electrode with an improved electroconductive skin-interface substrate, which will perform a similar function to, and eliminate the need for, an electrolyte solution, electrode paste or electrode gel.

Another objective of this invention is to provide an electrode with a skin-interface substrate having pressure sensitive adhesive properties which will enable the electrode to adhere to the skin without the use of tape or other securing mediums.

Another objective of this invention is to provide an adhesive substrate that has high tack so that minimal pressure is needed to apply it to the skin but is such that it can also be easily separable from the skin upon removal without any noticeable residue.

A further objective is to provide an electrode with a non-liquid skin-interface which is a film which will maintain a uniform thickness and will not separate to expose sections of a conductive support member to the skin.

An even further objective is to provide an electrode having a skin-interface substrate which will not decompose or dry out like electrodes utilizing electrolyte solutions under long periods of use.

Other objects and advantages of the instant invention will become apparent from a careful reading of the specification below.

SUMMARY OF THE INVENTION

The objectives of this invention are accomplished in a medical electrode, suitable for stimulation and monitoring applications, including an electrically conductive member capable of being connected to an external electro-medical apparatus. This conductive member may be a pliable sheet of material preferably having connected thereto a medium for securing positive electrical connection between the conductive member and the external electro-medical apparatus. Attached to the underside of the conductive member and extending away from the electrical connection is an electrically conductive skin-interface substrate material, preferable in the form of a film. This material must have adhesive properties so that it will adhere to the skin of a patient. Preferably, this material also has plastic and hydrophilic properties. A suitable combination of the aforementioned adhesive, plastic and hydrophilic properties is provided by an adhesive composition which comprises an electrical conductive organic polymer plasticized with a polyhydric alcohol, e.g., glycerol.

Suitable electrically conductive organic polymers useful in the adhesive composition utilized in the medical electrode of the present invention include copolymers derived from the polymerization of acrylic acid and N-vinylpyrrolidone. Such copolymer may further include the following comonomers: acrylamide, 2-acrylamido propane sulfonic acid and methylene-bis-acrylamide.

The adhesive composition may also include a thickener such as a copolymer of ethylene and maleic anhydride, or methylvinylether and maleic anhydride, or N-vinylpyrrolidone and acrylic acid, or N-vinylpyrrolidone and vinylacetate.

The precursor to said adhesive composition is copolymerized to yield a film having suitable adhesive properties and electroconductivity properties for use as a medical electrode adhesive in the presence of an ultraviolet sensitive curing agent such as 2-hydroxy-2-methyl-1-phenyl-propan-2-one (available as Darocure 1173®), 4-(2-hydroxyethoxy)-phenyl-(2-hydroxy-2-phenyl-(2-hydroxy-2-propyl)ketone (available as Darocure 2959®), or 2,2-dimethoxy-2-phenylacetophenone (available as Irgacure® 651).

BRIEF DESCRIPTION OF THE DRAWINGS

The invention will be more readily understood by reference to the drawings wherein like numerals refer to like elements and in which.

DETAILED DESCRIPTION OF THE INVENTION

Medical electrodes are intended for usage as efficient and effective transmission mediums between a patient's skin and an electro-medical apparatus. Primary to their operation is a uniform conductivity through the electrode itself and a uniform conductivity across the electrode skin-interface. Uniform conductivity through an electrode is most often interrupted by a non-uniformity in the electrode materials. Uniform conductivity across the electrode skin-interface is most often interrupted by a separation of some or all of the electrode interfacing material in contact with a patient's skin.

Preferably, the electrode is intended to be disposable. It is also intended to have adhesive properties sufficient to be self-adhering to a patient's skin for approximately 8–12 hours. However, it should contain sufficient flexibility and elasticity to move as a patient's skin moves while returning to original shape when permitted. Additionally, it is intended to provide uniform conductivity with even current densities of approximately 30 microamperes per square millimeter when subjected to a stimulus of about 60 milliamperes at 35 cycles per second having a pulse duration of about 250 microseconds. This electrode is intended to be easily handled, non-irritating to a patient's skin, and sterilizable.

Figure 1:
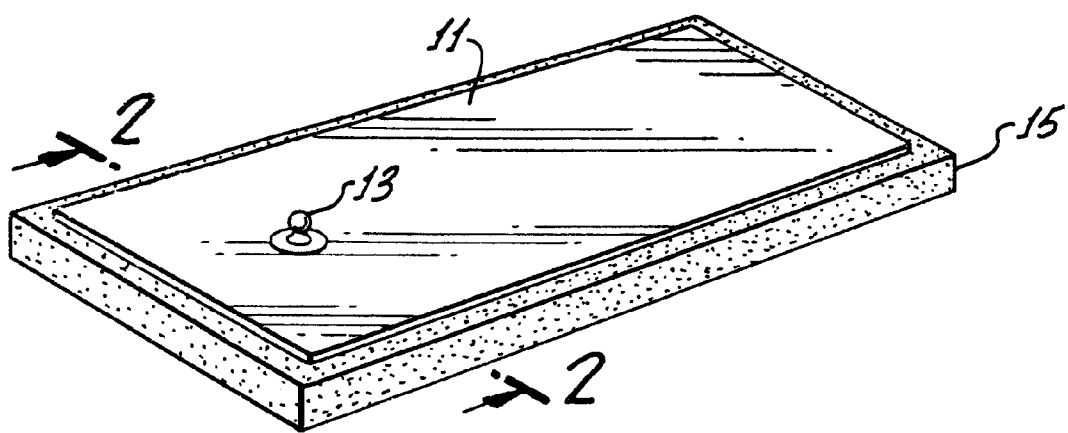
FIG. 1 shows a perspective view of the electrode.

The electrode configuration is shown in FIG. 1. A conductive member 11 is cut, stamped or otherwise shaped out of a piece of conductive material which may be aluminum foil or a polyester, e.g., a polyethylene terephtalate (Mylar®) coated with aluminum or tin. The shape to which this conductive member 11 is formed will depend upon the particular application in which it is to be used. The shape is sometimes round but may be as shown in FIG. 1, rectangularly shaped.

Alternately, other metallic foils, conductive polymers, graphitized or metalized cloth or wire mesh may be used as the conductive member. In particular, the knit conductive fabric disclosed in U.S. Pat. No. 4,722,354 may be utilized as the conductive member. For each material, an appropriate strength and thickness is to be chosen to yield a pliable, yet sufficiently strong member 11. When the conductive member 11 is of aluminum foil, it usually is of 1–10 mil thickness.

Secured to the outer surface of the conductive member 11 is a connector 13 for providing a medium to which external signal cables may be attached for electrically communicating with the conductive member 11. This connector 13 may be a conductive swaged snap fastenerer 13, as shown in the accompanying drawings, which is available commercially. This fastenerer 13 is mechanically and electrically attached to the conductive member 11, extending perpendicularly from the outer surface of this member 11. Alternatively, when the conductive member is a knit conductive fabric, the electrical connector may be stranded stainless steel as shown in U.S. Pat. No. 4,722,359.

Abutting the inner surface of the conductive member 11 is an electrically conductive skin-interface substrate 15. This substrate 15 is a layer of material being typically a film or sheet which will be described below.

The conductive substrate 15 is shaped correspondingly to the conductive member 11. When constructed in combination with a rectangular member 11, the substrate 15 is also rectangular. The film thickness of this substrate 15 is uniform throughout, however, this uniform film may be of various thicknesses. A range of 20 to 100 mils, e.g., about 50 mils is common.

As will be discussed below, the substrate 15 is a film or sheet having adhesive properties, thus when it is brought into contact with the conductive member 11, it will adhere to that member 11 providing electrical connection with it.

Figure 2:
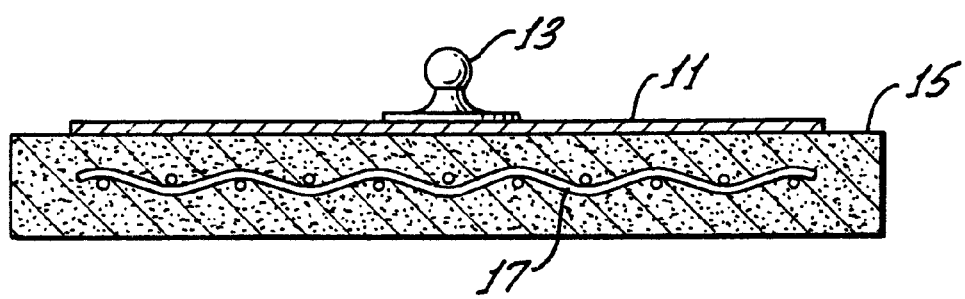
FIG. 2 shows a cross-section in side elevation through the electrode of FIG. 1.

A supporting scrim 15, FIG. 2 may be used in electrode configurations where a greater thickness substrate 15 film is used. This scrim 17, while not a necessary part of the electrode, will tend to support by being distributed throughout the substrate 15. A further advantage to the use of this scrim 17 is that it acts to reinforce and strengthen the substrate 15.

The scrim 17 is positioned midway through the thickness of the substrate 15, in alignment with the conductive member 11, and is of a size to extend completely under the conductive member 11. The scrim 17 can be a non-woven spun-bonded polyester fabric, a non-woven net of a stretched, embossed melt-extruded polymeric film, a non-woven sheet of polyolefin monofilaments heat-sealed together at their interstices or a thin sheet of a thermoplastic polymer with holes heat-stamped in a geometric pattern.

In operation, the electrode is applied with the substrate 15 in direct contact with the skin. The adhesive properties of the substrate 15 eliminate the necessity for tape or other securing mediums to hold the electrode in continuous contact with the skin. The swaged fastenerer 13, or other suitable connector, receives electrical signals from an external apparatus. These signals are conducted into the conductive member 11 which in turn directly conducts them into the substrate 15. In this manner, current densities are uniformly distributed over the area of the substrate 15 in contact with the conductive member 11 and, in turn, are uniformly transmitted to the skin surface in contact with the substrate 15.

Primary to the unique structure of the electrode for eliminating the need for added electrode pastes, gels or electrolyte solutions, and for eliminating the need for securing mediums to hold the electrode in place, are the composition and structure of the substrate 15 material, enabling it to possess the desired physical, chemical and electrical properties.

Substrate 15 is a sheet or film of an electrically conductive organic polymer plasticized with a polyhydric alcohol, preferably glycerol.

The electrically conductive organic polymers that are utilized in preparing substrate 15 are derived from the copolymerization of a mixture of monomeric acrylic acid and N-vinylpyrrolidone. Said organic polymer may comprise 25 to 75 parts per hundred, by weight (pph), e.g., 30 to 60 pph, acrylic acid and 2 to 30 pph, e.g. 10 to 30 pph, N-vinylpyrrolidone. In addition, the above mixture of comonomers, the organic polymer, may further include additional comonomers; in particular, 1 to 20 pph, e.g., 1 to 8 pph, acrylamide is desirable.

Furthermore, the organic polymer may comprise, e.g., 0.1 to 5 pph, e.g., about 2 pph, of a sulfonic acid-containing comonomer to (promote adhesion of the substrate), such as 2-acrylamide propane sulfonic acid (AMPS) and from, e.g., 0.1 to 5 pph, e.g., about 0.5 to 1.5 pph of a cross-linking agent, such as methylene-bis-acrylamide, to increase to molecular weight and cohesively of the conductive organic polymer through crosslinking. Other comonomers having at least two copolymerizable olefinic moeities, especially difunctional derivatives of acrylic acids, may be utilized in place of the preferred methylene bis-acrylamide). For example, polyethylene glycol dimethacrylates and diacrylates having a molecular weight of from about 200 to about 600 are suitable crosslinking agents.

In particular, it has been found that unexpectedly improved adhesion of the conductive organic polymer is obtained in an organic polymer, as described above, wherein the comonomer mixture includes both methylene-bis-acrylamide and acrylamide, for example, from about 0.1 to 0.5 pph of methylene-bis-acrylamide and from about 1 to 8 pph of acrylamide provide a substrate having unexpectedly improved adhesion.

The comonomer mixture that is copolymerized to provide the conductive organic polymer will also include a polyhydric alcohol, e.g., polyhydroxyhydrocarbons and oxyalkyls, e.g., ethyleneglycol, diethyleneglycol, glycerol, etc. to plasticize the organic polymer. The polyhydric functions as a humectant, i.e., it absorbs moisture and promotes conductivity of the substrate 15. The polyhydric alcohol may comprise from 25 to 75 pph, preferably from 40 to 60 pph, e.g., about 37 to 53 pph of the comonomer mixture. Most preferably, the polyhydric alcohol is glycerol.

The comonomer mixture that is copolymerized to provide the conductive organic polymer may also include a thickening agent. The thickening agent may be a high molecular weight polymer or copolymer such as a N-vinylpyrrolidone/vinylacetate copolymer (Luviskol VA 73W or VA 64W) available from BASF; methylvinylether/maleic acid copolymer (Gantrez® S95), which is available from ISP; ethylene/maleic anhydride (EMA) Copolymer, which is available from Zeeland Chemical; and N-vinylpyrrolidone/acrylic acid Acrylidone® (ACP-1041 or Acrylidone 1005), which is available from ISP, and may comprise from about 0.5 to 8 pph of the comonomer mixture, e.g., about 2 to 5 pph. It has unexpectedly been found that N-vinylpyrrolidone/acrylic acid at a concentration of from 0.5 to 2.5, for example from 0.5 to 1.5 pph provides a substrate having improved adhesion. It has also been unexpectedly found that N-vinylpyrrolidone/vinylacetate provides adhesion similar to N-vinylpyrrolidone/acrylic acid.

The above comonomer mixture is preferably copolymerized or cured by thermal or ultraviolet (UV) radiation. Therefore, an ultraviolet sensitive curing agent is provided in the comonomer mixture at a concentration of from 0.05 to 3 pph, preferably from 0.5 to 2.0 pph. Suitable curing agents are 2-hydroxy-2-methyl-1-phenyl-propan-2-one (available as Darocur 1173®), 4-(2-hydroxyethoxy)phenyl (2-hydroxy-2-phenyl-(2-hydroxy-2-propyl)ketone (available as Darocure 2959®), or 2,2-dimethoxy-2-phenyl acetophenone (available as Irgacure® 651), all of which are available from Ciba-Geigy.

Thus, to prepare the substrate 15, the following gelled comonomer mixtures may be subjected to thermal or ultraviolet polymerization conditions:

| Ingredient | Broad Range pph | Preferred Range pph |
|---|---|---|
| acrylic acid* | 15–30 | 18–26 |
| N-vinylpyrrolidone | 0.5–15 | 1–10 |
| acrylamide | 0–10 | 0.5–2 |
| methylene-bis-acrylamide | 0.01–2 | 0.03–0.1 |
| AMPS | 0.1–6 | 2–5 |
| thickener | 0.5–8 | 0.5–3.0 |
| glycerin | 25–75 | 37–53 |
| UV sensitive curing agent | 0.05–3 | 0.3–2.0 |
| distilled water | 5–25 | 8–25 |

The acrylic acid is preferably partially neutralized with a basic potassium or sodium oxide, hydroxide, or carbonate. For example, from 33 to 67 molar percent acrylic acid may be neutralized.

The above conductive substrate has a capacity for absorbing and retaining large amounts of water. This property further promotes the conductivity of the copolymer.

As previously mentioned, while the above disclosed substrate will absorb large amounts of water, it is substantially insoluble in water because the conductive organic polymer contains at least 0.02 parts by weight per 100 parts of monomer of a crosslinking agent.

The substrate 15 compositions exhibit a tackiness which can be increased as the glycerol concentration is increased. As water and/or salt water is absorbed, the surface of the substrate material 15 softens. As a result, the substrate 15 will flow into pores and other irregularities in the skin, creating a mechanical interlock bond with the skin in addition to the already present adhesive bond. The bonding and, concomitantly, the electrical transmission of the electrode are enhanced as it "ages" in contact with the skin.

The flow condition eliminates air spaces between the skin and the substrate 15 to greatly reduce the impedance across the interface. This in turn greatly reduces the heat normally created at this interface. While the surface portion of the substrate 15 will flow, the greater portion of its mass will remain intact. Thus, the material resists separation or the development of irregular thicknesses. As a result, two heat and/or burn producing conditions, i.e., a high resistance across the interface due to an air layer which creates high temperatures over the entire interface, and the physical contact of the conductive member 11 directly to the skin creating a shunt of the current to a small area and generating extreme temperature in that area, are avoided.

A secondary electrical effect is also improved as the electrode "ages." Present during the operation of all electrodes is a battery effect created at the skin interface due to the capacitance across this interface. This battery effect causes some current to tend to circle backward towards its source of flow creating eddy currents. With this electrode of the invention, as water and body salts are absorbed into the electrode substrate, the interface area becomes more ionically (i.e., electrically) homogenous, thus reducing the battery effect and any resulting eddy currents.

The electrode may be packaged for use in a sealed envelope of any of a number of suitable materials such as polyethylene or aluminum foil. A release paper or film of the waxed or plastic-coated type can be used to protect the substrate 15 before application to a skin surface.

The invention is further illustrated by the following examples which are illustrative of a specific mode of practicing the invention and is not intended as limiting the scope of the appended claims.

EXAMPLE I

The formulation designated as "A" in Table 1 is utilized to prepare the conductive substrate. This formulation is prepared as follows: Into a stainless steel mixing container, equipped with a mechanical stirrer, is added 153.7 g of deionized water. With slow agitation, 45.8 g of potassium hydroxide is slowly added to water. After allowing the stirred caustic solution to cool to room temperature, 200.0 g of glacial acrylic acid, 17.4 g of acrylamide, 520.0 g of glycerin and 0.6 g of methylene-bis-acrylamide, in that order, are slowly added to the aqueous solution. The resulting mixture is stirred for an additional 15 minutes while the solution is purged with a slow stream of nitrogen gas to displace the residual dissolved oxygen gas from the solution. Finally, a mixture of 44.75 g of N-vinylpyrrolidone and 0.75 g of Irgacure® 651 is poured into the stirred aqueous solution. The resulting mixture is coated on and penetrates a polyester scrim, such as Reemay® 1006 or 2250 to provide a coating thickness of between 25 to 100, e.g., about 40 to 60 mils. Typical line speeds for the coating process vary from 15 to 50, e.g., 20 to 40 linear feet per minute. The coated polyester scrim is irradiated with ultraviolet radiation from a UV source, such as the electrodeless microwave energy activated curing system available as the 1-600-M from Fusion Systems Corporation operating at from 400 to 600 watts/inch. The cured composition is subject to testing for adhesivity (i.e., the bond between the scrim reinforced gel and a substrate, e.g., a standard stainless steel plate or possibly the mylar film web upon which the scrim reinforced gel is coated prior to being irradiated), using the Satec T1000 material Testing Machine (SATEC Systems, Grove City, Pa.) equipped with an adjustable tilt table set for 90°. The test procedure for 90° peel strength required the pulling of a one-inch-wide strip of gel from the substrate (stainless steel plate or Mylar® web) at 12 inches/minute and at an angle of 90° to the plane of the sample as per ASTM D1876, ASTM D3330M (American Society for Testing Materials, Philadelphia, Pa.) or PSTC-1 and -3 (Pressure Sensitive Tape Council, Glenview, Ill.), and recording the average peel force in grams/one inch-width. (ASTM D3330M and PSTC-1 and -3 are for 180° peel testing but were adapted for use in this Example.) Formulations B through L are prepared similarly, except as specifically noted in Table 1.

The following results were obtained and reported in Table 1.

TABLE 1

| INGREDIENTS (WT-%)—/—FORMULATION# | A | B | C | D | E | F | F |
|---|---|---|---|---|---|---|---|
| ACRYLIC ACID[1] | 20.000 | 19.910 | 19.910 | 19.910 | 18.810 | 18.601 | 18.601 |
| POLYMER ADHESION/THICKENING | | | | | | | |
| AGENT    TYPE | 0.000 | 0.000 | 0.000 | [2]PAA | [3]MVE/MA | MVE/MA | MVE/MA |
|          AMOUNT | 0.000 | 0.000 | 0.000 | 0.000 | 0.160 | 0.417 | 0.417 |
| ACRYLAMIDE | 1.740 | 1.730 | 1.730 | 1.730 | 1.650 | 1.648 | 1.648 |
| METHYLENE-BIS-ACRYLAMIDE | 0.060 | 0.060 | 0.060 | 0.060 | 0.057 | 0.057 | 0.057 |
| AMPS | 2.000 | 1.990 | 1.990 | 2.000 | 1.890. | 1.895 | 1.895 |
| N-VINYLPYRROLIDONE | 4.475 | 4.360 | 4.360 | 4.350 | 4.150 | 4.144 | 4.144 |
| IRGACURE-651 | 0.075 | 0.075 | 0.0701 | 0.070 | 0.095 | 0.0951 | 0.095 |
| GLYCERIN | 52.000 | 51.770 | 51.760 | 51.760 | 49.30 | 49.258 | 49.258 |
| DISTILLED WATER | 15.370 | 15.650 | 15.650 | 15.650 | 20.860 | 20.849 | 20.849 |
| KOH (or NaOH) | 4.560 | 4.4601 | 4.460 | 4.460 | 3.030 | 3.036 | 3.036 |
| UV SOURCE (WATTS) | 600/400 | 600/400 | 600/400 | 600/400 | 600/400 | 600/400 | 400/400 |
| CONTACT TIME/LINE SPEED (FT/MIN) | 14.000 | 14.000 | 14.000 | 14.000 | 14.000 | 14.000 | 35.000 |
| THICKNESS (MILS) | 45 ± 5 | 53 ± 5 | 90 ± 7 | 73 ± 17 | 80 ± 12 | 70 ± 13 | 32 ± 6 |
| pH-VALUE - HYDROGEL | 4.91 | 4.51 | | 4.30 | 4.35 | 4.41 | 4.30 |
| PEEL STRENGTH (G/1"-WIDTH) | 483 ± 60 | 639 ± 58 | 919 ± 114 | 925 ± 97 | 619 ± 144 | 894 ± 72 | 470 ± 35 |

| INGREDIENTS (WT-%)—/—FORMULATION | G | G | H | H | I | I |
|---|---|---|---|---|---|---|
| ACRYLIC ACID[1] | 18.963 | 18.963 | 18.961 | 18.961 | 18.893 | 18.893 |
| POLYMER ADHESION/THICKENING | | | | | | |
| AGENT    TYPE | MVE/MA | MVE/MA | MVE/MA | MVE/MA | MVE/MA | MVE/MA |
|          AMOUNT | 0.425 | 0.425 | 0.425 | 0.425 | 0.424 | 0.424 |
| ACRYLAMIDE | 1.681 | 1.681 | 1.681 | 1.681 | 0.000 | 0.000 |
| METHYLENE-BIS-ACRYLAMIDE | 0.058 | 0.058 | 0.058 | 0.058 | 0.158 | 0.158 |
| AMPS | 0.000 | 0.000 | 0.000 | 0.000 | 1.925 | 1.925 |
| N-VINYLPYRROLIDONE | 4.235 | 4.235 | 4.235 | 4.235 | 4.209 | 4.209 |
| IRGACURE-651 | 0.097 | 0.097 | 0.097 | 0.097 | 0.096 | 0.096 |
| GLYCERIN | 50.216 | 50.216 | 50.211 | 50.211 | 50.034 | 50.034 |
| DISTILLED WATER | 21.246 | 21.246 | 21.244 | 21.244 | 21.178 | 21.178 |
| KOH (or NaOH) | 3.090 | 3.090 | 3.089 | 3.089 | 3.084 | 3.084 |
| UV SOURCE (WATTS) | 600/400 | 600/400 | 600/400 | 400/400 | 600/400 | 400/400 |
| CONTACT TIME/LINE SPEED (FT/MIN) | 15.000 | 20.000 | 14.000 | 35.000 | 14.000 | 35.000 |
| THICKNESS (MILS) | 56 ± 6 | 66 ± 5 | 76 ± 23 | 47 ± 12 | 75.8 ± 7.4 | 60.0 ± 11.2 |
| pH-VALUE - HYDROGEL | 4.62 | 4.70 | 4.61 | 4.55 | 4.48 | 4.45 |
| PEEL STRENGTH (G/1"-WIDTH) | 669 ± 91 | 722 ± 130 | 754 ± 290 | 217 ± 21 | 149.6 ± 38.6 | 13.7 ± 24.2 |

TABLE 1-continued

| INGREDIENTS (WT-%)—/—FORMULATION | J | J | K | K | L | L |
|---|---|---|---|---|---|---|
| ACRYLIC ACID[1] | 18.928 | 18.928 | 19.184 | 19.184 | 18.898 | 18.898 |
| POLYMER ADHESION/THICKENING AGENT | | | | | | |
| TYPE | MVE/MA | MVE/MA | MVE/MA | MVE/MA | MVE/MA | MVE/MA |
| AMOUNT | 0.425 | 0.425 | 0.433 | 0.4331 | 0.424 | 0.424 |
| ACRYLAMIDE | 1.743 | 1.743 | 0.000 | 0.000 | 0.000 | 0.000 |
| METHYLENE-BIS-ACRYLAMIDE | 0.158 | 0.158 | 0.158 | 0.059 | 0.058 | 0.058 |
| AMPS | 0.000 | 0.000 | 0.000 | 0.000 | 2.000 | 2.000 |
| N-VINYLPYRROLIDONE | 4.217 | 4.217 | 4.296 | 4.2961 | 4.210 | 4.210 |
| IRGACURE-651 | 0.096 | 0.096 | 0.098 | 0.0981 | 0.096 | 0.096 |
| GLYCERIN - - | 50.126 | 50.126 | 51.068 | 51.068 | 50.046 | 50.046 |
| DISTILLED WATER | 21.217 | 21.217 | 21.615 | 21.615 | 21.183 | 21.183 |
| KOH (or NaOH) | 3.090 | 3.090 | 3.148 | 3.148 | 3.085 | 3.085 |
| UV SOURCE (WATTS) | 600/400 | 400/400 | 600/400 | 400/400 | 600/400 | 400/400 |
| CONTACT TIME/LINE SPEED (FT/MIN) | 14.000 | 35.000 | 14.000 | 35.000 | 14.000 | 35.000 |
| THICKNESS (MILS) | 97.2 ± 15.1 | 66.4 ± 5.4 | 60 ± 11 | 43 ± 6 | 66 ± 14 | 42 ± 5 |
| pH-VALUE - HYDROGEL | 4.61 | 4.56 | 4.51 | 4.53 | 4.41 | 4.43 |
| PEEL STRENGTH (G/1"-WIDTH) | 80.2 ± 36.6 | 37.4 ± 10.5 | 314 ± 85 | 226 ± 32 | 436 ± 72 | 349 ± 19 |

[1]The acrylic acid is partially neutralized.

As shown in Table 1, increasing the line speed from 14 to 35 linear feet per min, as shown for Formulations, F, H, I, J, K and L, resulted in a decrease in coating thickness and also a decrease in adhesivity. (Note that increasing the line speed from 15 to 20 linear feet per minute also had the same result, although the difference was diminished in this instance. See Formulation G.) Also, while not shown, Formulations similar to those shown in Table 1, wherein the crosslinking agent, methylene bis-acrylamide were absent, showed effectively no adhesivity, while Formulations I and J, wherein the crosslinking agent concentration was at 0.15 as compared to Formulations F, H, K and L wherein the crosslinking agent concentration was about 0.06 pph showed inferior adhesivity.

Nevertheless, the results in Table 1 clearly show unexpectedly improved adhesivity, wherein the gel mixture comprises up to 3 pph, e.g., from about 0.5 to 2 pph, acrylamide, and from about 0.03 to about 0.1, e.g., about 0.06 pph, methylene bis-acrylamide.

EXAMPLE II

This Example is carried out as discussed above for Example I, except that the formulations tested differ, as described in Table 2 below.

TABLE 2

| INGREDIENTS (WT-%)—/—FORMULATION# | M | M | M | M | N | O | P |
|---|---|---|---|---|---|---|---|
| ACRYLIC ACID | 20.000 | 20.000 | 20.000 | 20.000 | 20.000 | 20.000 | 20.000 |
| POLYMER ADHESION/THICKENING AGENT | | | | | | | |
| TYPE | [1]NVP/AA | NVP/AA | NVP/AA | NVP/AA | [2]MVE/MA | [3]EMA | NVP/AA |
| AMOUNT | 1.000 | 1.000 | 1.000 | 1.000 | 1.000 | 1.000 | 1.000 |
| AMPS | 4.000 | 4.000 | 4.000 | 4.000 | 2.000 | 2.000 | 2.000 |
| N-VINYLPYRROLIDONE | 4.000 | 4.000 | 4.000 | 4.000 | 4.000 | 4.000 | 4.000 |
| IRGACURE-2959 | 0.200 | 0.200 | 0.200 | 0.200 | 0.200 | 0.200 | 0.200 |
| DAROCURE-1173 | 0.200 | 0.200 | 0.200 | 0.200 | 0.200 | 0.200 | 0.200 |
| GLYCERIN | 40.000 | 40.000 | 40.000 | 40.000 | 45.000 | 45.000 | 45.000 |
| DISTILLED WATER | 24.500 | 24.500 | 24.500 | 24.500 | 21.500 | 21.500 | 21.500 |
| NaOH | 6.000 | 6.000 | 6.000 | 6.000 | 6.000 | 6.000 | 6.000 |
| HIGHLINK-AA4 | 0.100 | 0.100 | 0.100 | 0.100 | 0.100 | 0.100 | 0.100 |
| TOTAL | 100.000 | 100.000 | 100.000 | 100.000 | 100.000 | 100.000 | 100.000 |
| THICKNESS (MILS) | 48.4 | 52.4 | 49.1 | 50.3 | 46.6 | 32.0 | 34.8 |
| IMPEDANCE (OHM-CM) | | | | | 2604 | 5258 | 3350 |
| PEEL STRENGTH RATIO: MYLAR:PE | 0.7 | 1.3 | 1.3 | 2.0 | 0.2 | 0.7 | 0.5 |
| 90° PEEL STRENGTH(G/1"-WIDTH) - T.L. | 619 | 479 | 438 | 338 | 296 | 146 | 593 |
| 90° PEEL STRENGTH(G/1% WIDTH) - B.L. | 404 | 607 | 588 | | 72.3 | 105 | 274 |

| INGREDIENTS (WT-%)—/—FORMULATION# | Q | R | S | T | U | V | W | X |
|---|---|---|---|---|---|---|---|---|
| ACRYLIC ACID | 20.000 | 20.000 | 20.000 | 20.000 | 20.000 | 20.000 | 20.000 | 20.000 |
| POLYMER ADHESION/THICKENING AGENT | | | | | | | | |
| TYPE | NVP/AA | NVP/AA | NVP/AA | NVP/AA | EMA | EMA | EMA | EMA |
| AMOUNT | 1.000 | 1.000 | 1.000 | 1.000 | 1.000 | 1.000 | 1.000 | 1.000 |
| AMPS | 2.000 | 4.000 | 2.000 | 4.000 | 2.000 | 4.000 | 2.000 | 2.000 |
| N-VINYLPYRROLIDONE | 4.000 | 4.000 | 8.000 | 4.000 | 4.000 | 4.000 | 8.000 | 4.000 |
| IRGACURE-2959 | 0.200 | 0.200 | 0.200 | 0.200 | 0.200 | 0.200 | 0.200 | 0.200 |
| DAROCURE-1173 | 0.200 | 0.200 | 0.200 | 0.200 | 0.200 | 0.200 | 0.200 | 0.200 |
| GLYCERIN | 40.000 | 40.000 | 40.000 | 40.000 | 40.000 | 40.000 | 40.000 | 40.000 |
| DISTILLED WATER | 26.500 | 24.500 | 22.500 | 24.500 | 26.500 | 24.500 | 22.500 | 20.500 |

TABLE 2-continued

| INGREDIENTS (WT-%)—/—FORMULATION# | | | | | | | | |
|---|---|---|---|---|---|---|---|---|
| NaOH | 6.000 | 6.000 | 6.000 | 6.000 | 6.000 | 6.000 | 6.000 | 6.000 |
| HIGHLINK-AA[4] | 0.100 | 0.100 | 0.100 | 0.100 | 0.100 | 0.100 | 0.100 | 0.100 |
| TOTAL | 100.00 | 100.0 | 100.0 | 100.0 | 100.0 | 100.0 | 100.0 | 100.0 |
| THICKNESS (MILS) | 45.1 | 46.3 | 40.4 | 37.1 | 50.5 | 46.1 | 38.2 | 38.9 |
| IMPEDANCE (OHM-CM) | 2132 | 1146 | 1559 | 2427 | 3726 | 4202 | 2801 | 2110 |
| PEEL STRENGTH RATIO: MYLAR:PE | 2.4 | 2.6 | 3.7 | 3.6 | 0.8 | 0.9 | 0.9 | 0.8 |
| 90° PEEL STRENGTH(G/1"-WIDTH), T.L. | 177 | 209 | 170 | 117 | 137 | 90.3 | 92.1 | 1.5 |
| 90° PEEL STRENGTH(G/1% WIDTH) - B.L. | 423 | 538 | 630 | 424 | 115 | 83.0 | 79.4 | 89.4 |

| INGREDIENTS (WT-%)—/—FORMULATION# | Y | Z | AA | AB | AC |
|---|---|---|---|---|---|
| ACRYLIC ACID | 20.000 | 20.000 | 20.000 | 20.000 | 20.000 |
| POLYMER ADHESION/THICKENING AGENT | | | | | |
| TYPE | NONE | [1]NVP/AA | [5]NVP/AA | [6]VP/VA 70:30 | [7]VP/VA 60:40 |
| AMOUNT | 0 | 2.75 | 2.75 | 2.75 | 2.75 |
| AMPS | 4.000 | 4.000 | 4.000 | 4.000 | 4.000 |
| N-VINYLPYRROLIDONE | 4.000 | 4.000 | 4.000 | 4.000 | 4.000 |
| IRGACURE-2959 | 0.200 | 0.200 | 0.200 | 0.200 | 0.200 |
| DAROCURE-1173 | 0.200 | 0.200 | 0.200 | 0.200 | 0.200 |
| GLYCERIN | 40.000 | 40.000 | 40.000 | 40.000 | 40.000 |
| DISTILLED WATER | 22.750 | 22.750 | 22.750 | 22.750 | 22.750 |
| NaOH | 6.000 | 6.000 | 6.000 | 6.000 | 6.000 |
| HIGHLINK-AA4 | 0.100 | 0.100 | 0.100 | 0.100 | 0.100 |
| TOTAL | 97.25 | 100.0 | 100.0 | 100.0 | 100.0 |
| THICKNESS (MILS) | 49 | 44 | 54 | 46 | 50 |
| IMPEDANCE (OHM-CM) | 2419 | 2676 | 2710 | 2284 | 2411 |
| PEEL STRENGTH RATIO: MYLAR:PE | 1.7 | 1.1 | 1.6 | 1.7 | 1.9 |
| 90° PEEL STRENGTH(G/1"-WIDTH) T.L. | 622 | 720 | 1087 | 917 | 870 |
| 90° PEEL STRENGTH(G/1% WIDTH), T.L. | 362 | 664 | 689 | 530 | 467 |

[1]N-vinylpyrrolidone/acrylic acid copolymer (Acrylidone ® ACP-1041).
[2]Gantrez ® 595.
[3]Ethylene Maleic anhydride copolymer (available from Zeeland Chemical)
[4]Diacrylamidoacetic acid (available from Hoechst Celanese)
[5]N-vinylpyrrolidone/acrylic acid copolymer 250,000 MW (Acrylidone 1005)
[6]N-vinylpyrrolidone/vinyl acetate 70:30 ratio (Luviskol VA73W from BASF)
[7]N-vinylpyrrolidone/vinyl acetate 60:40 ratio (Luviskol VA64W from BASF)

The process of preparing the samples of this Example, the scrim is drawn through a trough of feedmix or monomer syrup and out through an aperture and under a doctor blade or gate adjusted to vary the thickness of the coating onto a 5-mil Mylar® polyester web, which immediately passes at a line speed of 20 linear feet per minute under the first of two 600 watts/in UV lamp irradiators. The web moves to a take-up station and a 2.5-mil polyethylene film is attached prior to rolling up the hydrogel sheet on a 6" core.

The peel strength or adhesivity of the cured hydrogel on the Mylar® side and on the polyethylene side is measured off of a stainless steel plate. The significance of the two peel strength values are important as they are measures of how well the hydrogel sheet will bond to the conductive or metallic dispersive element (the polyethylene film side) and to the patient (the Mylar® film side). Other factors being equal, the ratio of these two peel strengths also relates to the ratio of the gel thicknesses on each side of the scrim. Generally, it is preferred to have the peel strength on the Mylar® film side to be higher than the peel strength on the polyethylene film side.

The volume resistivity or bulk impedance is measured using a Hewlett Packard Model 4800A Vector Impedance Meter. Circles, which are 1.128 inches in diameter or 1-inch square in surface area and known thicknesses, are cut from the hydrogel sheet. The circle is placed between two stainless steel polished plates having 1-inch square surface area. Each plate is connected to the input leads of the meter and the impedance determined at a frequency of 1,000 Hz. The impedance in ohms is multiplied by the surface area in squared centimeters of the gel and divided by the thickness of the gel in centimeters. The volume resistivity is reported as ohm-cm.

It is clear from the results reported that the N-vinylpyrrolidone acrylic acid copolymer provides improved adhesion as compared to the other thickeners when compared at equal concentrations of N-vinylpyrrolidone monomer, AMPS and glycerine concentration. In particular compare Formulations Q and U, R and V, S and W, T and X, and P, O and N.

In addition, the N-vinylpyrrolidone/vinylacetate copolymer thickener is substantially equivalent to N-vinylpyrrolidone/acrylic acid thickener in improving the adhesion of the conductive layer. Compare Formulations AB and AC with Formulations Z and AA. Also, the peel strength ratio of the N-vinylpyrrolidone thickener-containing conductive polymer is equal or better than the peel strength ratio of the N-vinylpyrrolidone/acrylic acid thickener-containing conductive polymer.

While particular embodiments of the invention have been described, it will be understood, of course, that the invention is not limited thereto since many obvious modifications can be made and it is intended to include within this invention any such modifications as will fall within the scope of the appended claims. For example, it will be appreciated, by those skilled in the art, that other carboxylic substituted vinyl or propenyl monomers may be substituted for acrylic acid, e.g., methacrylic acid, crotonic acid, isocrotonic acid, itaconic acid, maleic acid, fumaric acid or their half ester/acid derivatives.

Other alkaline materials can be utilized to neutralize the acrylic acid monomer, e.g., mono and poly positive alkaline materials, e.g., sodium, potassium, calcium, magnesium, aluminum basic oxides, hydroxides or carbonates may be used as well as ammonium hydroxide, etc.

Other copolymerizable N-vinyl lactam monomers may be substituted for N-vinylpyrrolidone, e.g., N-vinyl-ε-caprolactam or N-vinylbutyrolactam.

Other plasticizers and/or humectants may be substituted for glycerol including urea and the polyhdroxyorganics described above.

Other thickeners or viscosity increasing agents which may be used in the medical electrodes of the present invention include polyacrylamide, polyvinyl alcohol, polyacrylic acid, polyethylene oxide, methyl cellulose, ethyl cellulose, carboxymethyl cellulose, hydroxyethyl cellulose and polyacrylamidealkylsulfonic acid.

Finally, the conductive polymer may include particulate reinforcing agents and/or fillers, such as silica, e.g. Cabosil®.

What is claimed:

1. An electrode providing electrical contact with a patient's skin comprising:
   a conductive member including means for connection to an external electrical apparatus; and
   means for electrically interfacing to said patient's skin being electrically and mechanically connected to said conductive member, said interfacing means being a non-liquid film and which comprises an electrically conductive organic polymer plasticized with a polyhydric alcohol with said organic polymer being derived from a monomeric mixture comprising from about 15 to 30 pph acrylic acid, 0.5 to 30 pph N-vinylpyrrolidone and 0.01 to 2 pph of a crosslinking agent and from about 0.5 to 8 pph of a thickening agent comprising N-vinylpyrrolidone/vinylacetate copolymers.

2. The electrode of claim 1 wherein said polyhydric alcohol is glycerol.

3. The electrode of claim 2 wherein said crosslinking agent is selected from the group consisting of methylene bis-acrylamide and polyethylene glycol acrylates and diacrylates having a molecular weight from about 200 to about 600.

4. The electrode of claim 3 wherein said monomeric mixture further comprises from about 0.1 to 6 pph of a sulfonic acid-containing comonomer.

5. The electrode of claim 3 wherein said monomeric mixture further comprising from about 0.5 to 2 pph acrylamide.

6. The electrode of claim 5 comprising from 0.5 to 2 pph of acrylamide and from 0.03 to 0.1 pph methylene bis-acrylamide.

7. The electrode of claim 5 wherein said monomeric mixture further comprises from about 40 to 60 pph of glycerol.

8. The electrode of claim 7 wherein said sulfonic-acid-containing comonomer is 2-acrylamido propane sulfonic acid.

9. The electrode of claim 1 wherein said monomeric mixture further comprises from 0.05 to 3 pph of an ultraviolet sensitive curing agent.

10. The electrode of claim 9 wherein said ultraviolet sensitive curing agent is selected from the group consisting of 2-hydroxy-2-methyl-1-phenylpropan-2-one 4-(2-hydroxyethoxy)phenyl (2-hydroxy-2-phenyl-2-hydroxy-2-propyl)ketone or 2,2-dimethoxy-2-phenyl-acetophenone and mixtures thereof.

11. The electrode of claim 1 wherein said monomeric mixture comprises from about 2 to 5 pph of a thickening agent comprising a N-vinylpyrrolidone/vinyl acetate copolymer.

12. The electrode of claim 1 wherein said monomeric mixture comprises from about 0.5 to 2.5 pph of a thickening agent comprising a N-vinylpyrrolidone/vinyl acetate copolymer.

13. The electrode of claim 1 wherein said mixture comprises from about 0.5 to 1.5 pph of a thickening agent comprising a N-vinylpyrrolidone/vinyl acetate copolymer.

14. The electrode of claim 1 wherein said N-vinylpyrrolidone/vinyl acetate copolymer is selected from the group consisting of copolymers having a vinylpyrrolidone/vinylacetate ratio of 70:30 and copolymers having a vinlypyrrolidone/vinylacetate ratio of 60:40.

15. The electrode of claim 1 wherein said monomeric N-vinylpyrrolidone/vinylacetate copolymer comprises from about 50 to 80 pph N-vinylpyrrolidone and from about 50 to 20 pph vinylacetate.

16. An electrode providing electrical contact with a patient's skin comprising:
   a conductive member including means for connection to an external electrical apparatus; and means for electrically interfacing to said patient's skin being electrically and mechanically connected to said conductive member, said interfacing means being a non-liquid film which is easily separable from the skin upon removal without any noticeable residue and which consists essentially of an electrically conductive organic polymer plasticized with a polyhydric alcohol with said organic polymer being derived from a monomeric mixture comprising from about 15 to 30 pph acrylic acid, 0.5 to 15 pph N-vinylpyrrolidone, 0.5 to 2 pph acrylamide and 0.03 to 0.1 pph methylene bis-acrylamide and from about 0.5 to 8 pph of a thickening agent comprising a N-vinylpyrrolidone copolymer; providing however, the vinylpyrrolidone copolymer is not a N-vinylpyrrolidone/acrylic acid copolymer.

17. The electrode of claim 16 wherein said polyhydric alcohol is glycerol.

18. The electrode of claim 17 wherein said monomeric mixture further comprises from about 0.1 to 5 pph of a sulfonic-acid-containing comonomer.

19. The electrode of claim 18 wherein said sulfonic acid-containing comonomer is 2-acrylamide propane sulfonic acid.

20. The electrode of claim 19 wherein said monomeric mixture further comprises from 0.05 to 3 pph of an ultraviolet sensitive curing agent.

21. The electrode of claim 20 wherein said ultraviolet sensitive curing agent is selected from the group consisting of 2-hydroxy-2-methyl-1-phenyl-propan-2-one 4-(2-hydroxyethoxy)phenyl (2-hydroxy-2-phenyl-(2-hydroxy-2-propyl) ketone or 2,2-dimethoxy-2phenyl-acetophenone and mixtures therefor.

22. The electrode of claim 20 wherein said monomeric mixture comprises from 40 to 60 pph glycerol.

* * * * *